(12) United States Patent
Alexander et al.

(10) Patent No.: US 7,974,704 B2
(45) Date of Patent: Jul. 5, 2011

(54) LEAD BODY CONSTRUCTIONS FOR IMPLANTABLE MEDICAL ELECTRICAL LEADS

(75) Inventors: James A. Alexander, Shorewood, MN (US); Loren S. Chapeau, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 986 days.

(21) Appl. No.: 11/843,021

(22) Filed: Aug. 22, 2007

(65) Prior Publication Data

US 2009/0054949 A1 Feb. 26, 2009

(51) Int. Cl.
*A61N 1/05* (2006.01)
(52) U.S. Cl. .................................. 607/116; 607/115
(58) Field of Classification Search ........... 607/115–129
See application file for complete search history.

(56) References Cited

U.S. PATENT DOCUMENTS

| | | | |
|---|---|---|---|
| 4,172,451 A | 10/1979 | Kline | |
| 4,379,462 A | 4/1983 | Borkan et al. | |
| 4,944,088 A | 7/1990 | Doan et al. | |
| 5,466,253 A | 11/1995 | Doan | |
| 5,876,430 A | 3/1999 | Shoberg et al. | |
| 5,935,159 A | 8/1999 | Cross, Jr. et al. | |
| 6,096,069 A | 8/2000 | Bischoff | |
| 6,434,430 B2 * | 8/2002 | Borgersen et al. | 607/122 |
| 7,130,699 B2 * | 10/2006 | Huff et al. | 607/116 |
| 2002/0183824 A1 | 12/2002 | Borgersen et al. | |
| 2004/0215300 A1 | 10/2004 | Verness | |
| 2005/0137665 A1 | 6/2005 | Cole | |
| 2007/0225784 A1 * | 9/2007 | Bly et al. | 607/116 |

FOREIGN PATENT DOCUMENTS

WO 9706727 A1 2/1997

OTHER PUBLICATIONS

PCT/US2008/071977, International Search Report and Written Opinion, dated Dec. 12, 2008, 17 pages.

* cited by examiner

*Primary Examiner* — Carl H Layno
*Assistant Examiner* — Brian T Gedeon (57) ABSTRACT

A lead body of an implantable medical electrical lead includes a first filler and a second filler, each extending within a proximal portion thereof. The first filler may have a stiffness that is less than that of the second filler, and may surround and isolate a plurality of conductors which are coupled to a connector terminal of the lead, which connector terminal extends proximally from a proximal end of the lead body. The second filler extends along a limited length, alongside the first filler, wherein the limited length extends distally from the connector terminal; the second filler may further extend into the connector terminal.

46 Claims, 5 Drawing Sheets

LEAD BODY CONSTRUCTIONS FOR IMPLANTABLE MEDICAL ELECTRICAL LEADS

TECHNICAL FIELD

The present disclosure pertains to implantable medical systems and more particularly to lead body constructions for implantable medical electrical leads.

BACKGROUND

The medical device industry produces a variety of implantable medical device systems that provide electrical stimulation therapy to patients suffering from cardiac and/or neurological disorders. Examples of these implantable systems include those providing cardiac pacing and/or defibrillation, and those providing neuromodulation. Electrical stimulation is typically delivered through one or more electrodes of a stimulation lead, implanted in intimate contact with tissue at specific sites, for example, in contact with myocardial, spinal cord, peripheral nerve, or brain tissue; the one or more electrodes are coupled to a stimulation source, or device, which is implanted in a subcutaneous pocket, by corresponding isolated conductors that extend, within an elongate insulative lead body, from the device, in the pocket, to the electrodes, at the stimulation site. The conductors are typically coupled to the device via a connector terminal, which is designed for reversible connection within a connector port of the device and that extends proximally from a proximal end of the elongate lead body.

Because the subcutaneous pocket for the device implant is typically somewhat remote from the stimulation site, elongate insulative lead bodies are designed to have a sufficient length, flexibility and durability to be routed through and/or around anatomical structures, between the pocket and the stimulation site, and to protect and isolate the conductors and electrodes of the lead from one another and from the implant environment. In some cases another lead, including an additional set of conductors, an associated lead body, a connector port, and a connector terminal, is included in the system, either to extend a length of the stimulation lead, or to convert the connector of the stimulation lead to another type of connector, which is compatible with a particular type of device connector port.

Lead connector terminals are typically coupled to device connector ports, as well as to connector ports of other leads, by grasping the associated lead body in proximity to the connector terminal and inserting the connector terminal into the port.

BRIEF DESCRIPTION OF THE DRAWINGS

The following drawings are illustrative of particular embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

Various lead body constructions, which have enhanced stiffness to increase an ease of insertion for connector terminals have been described in the art, however there is still a need for new lead body constructions that provide the requisite stiffness without complicating methods for connector assembly and without compromising the flexibility and durability of the corresponding lead.

The following detailed description is exemplary in nature and is not intended to limit the scope, applicability, or configuration of the invention in any way. Rather, the following description provides practical illustrations for implementing exemplary embodiments. Examples of constructions, materials, dimensions, and manufacturing processes are provided for selected elements, and all other elements employ that which is known to those of skill in the field of the invention. Utilizing the teaching provided herein, those skilled in the art will recognize that many of the examples have suitable alternatives that can be utilized.

Figure 1:
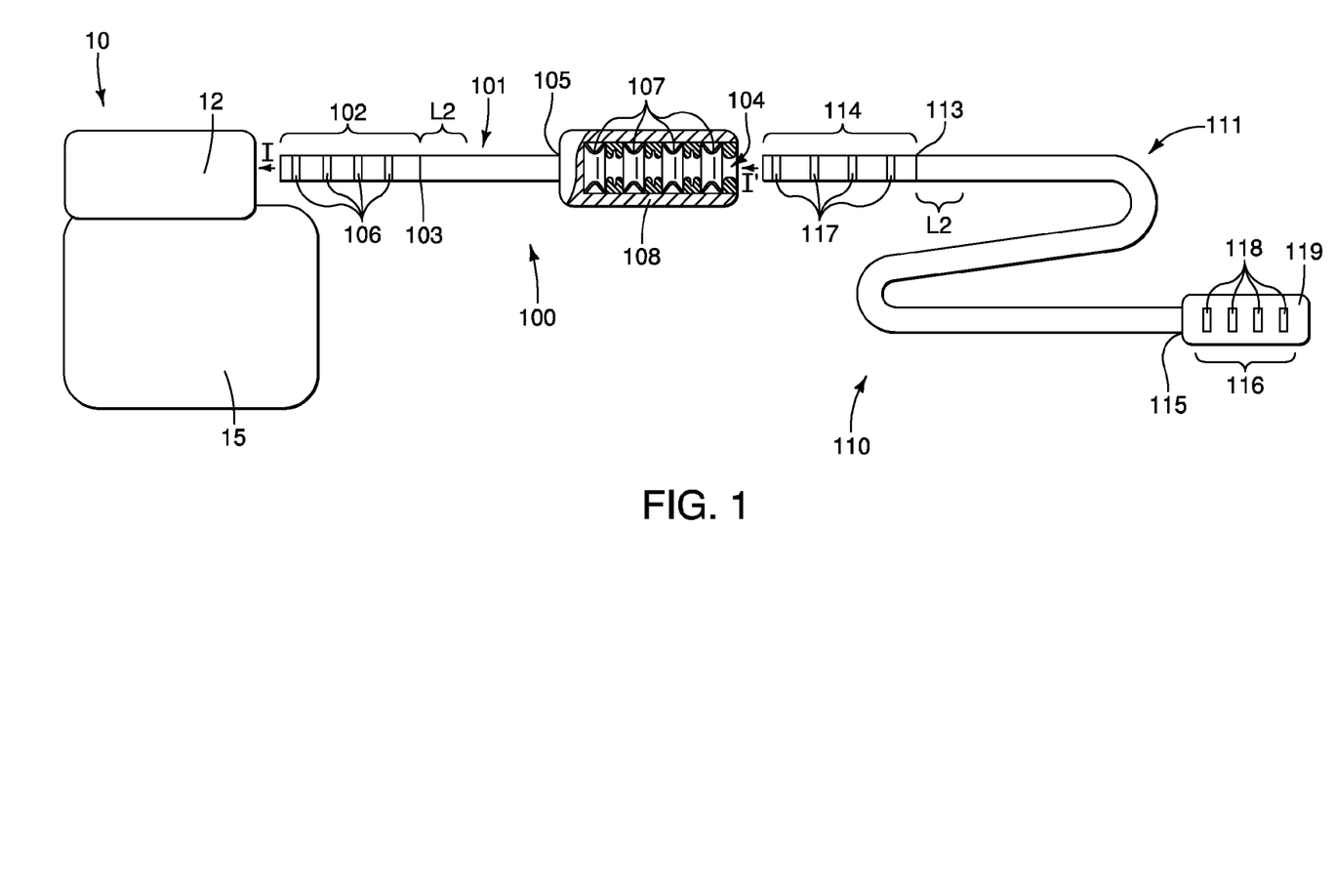
FIG. 1 is a plan view of an exemplary system which may employ embodiments of the present disclosure.

FIG. 1 is a plan view of an exemplary implantable medical electrical system which may employ embodiments of the present disclosure. FIG. 1 illustrates the system including an implantable medical device 10, and a lead system formed by an adapter lead 100 and a stimulation lead 110. Adapter lead 100 may be employed to extend a length of lead 110 and/or to convert a connector terminal 114 of lead 110 to a different connector terminal 102 for compatibility with a connector port (not shown) of a connector module 12 of device 10. Those skilled in the art will appreciate that connector module 12 contains electrical contacts, within the port thereof, which are adapted to mate with individual connector elements 106 of connector terminal 102, and/or with individual connector elements 117 of connector terminal 114 (if terminal 114 is compatible with the device connector port), and that hermitically sealed feedthrough assemblies couple each of the electrical contacts of connector module 12 with a power supply and electronic circuitry contained within a housing 15 of device 10. Those skilled in the art will further appreciate that connector elements 106, of connector terminal 102, are isolated from one another by insulative spacers extending therebetween; likewise, connector elements 117, of connector terminal 114, are isolated from one another by corresponding insulative spacers. It should be noted that, although the illustrated in-line configuration of connector terminals 102 and 114, which is generally known to those skilled in the art, is employed by some embodiments of the present disclosure, the invention is not so limited, and alternate embodiments may include any other type of connector terminal configuration.

FIG. 1 further illustrates stimulation lead 110 and adapter lead 100 each including an elongate insulative lead body 111 and 101, respectively; stimulation lead body 111 includes a proximal end 113, from which connector terminal 114 extends, and a distal end 115, from which an electrode array 116 extends; and adapter lead body 101 includes a proximal end 103, from which connector terminal 102 extends, and a distal end 105, from which a connector port 104 extends. Electrode array 116 is shown including a plurality of electrodes 118, which are isolated from one another, being mounted on an insulative member 119; each electrode 118 is coupled to a corresponding connector element 117, via a corresponding isolated conductor 215 (FIGS. 2-3) that extends within lead body 111, between proximal end 113 and distal end 115. Connector port 104 is shown extending within an insulative housing 108 and including a plurality of electrical contacts 107, which are isolated from one another, for example, by internal sealing rings, which are known to those skilled in the art; each contact 107 is coupled to a corresponding connector element 106, via a corresponding isolated conductor 215 that extends within lead body 101, between proximal end 103 and distal end 105. Any suitable components and construction methods, which are known to those skilled in the art, may be employed to manufacture electrode array 116, connector terminals 102, 114, and connector port 104 and to couple these elements to the ends of the corresponding lead body; some exemplary construction methods will be described, below, in conjunction with FIGS. 4A-B, for connector terminals 102, 114, according to some embodiments of the invention.

With further reference to FIG. 1, connector terminal 102 of adapter lead 100 may be inserted, per arrow I, into the port of module 12 for electrical coupling with device 10, and connector terminal 114 of stimulation lead 110 may be inserted, per arrow I', into port 104 of adapter lead 100, for electrical coupling with device 10, via adapter lead 100, by the mating of each connector element 117 with a corresponding electrical contact 107 mounted within port 104. Either one or both of leads 100, 110 may employ any of the lead body constructions disclosed herein, in order to facilitate the corresponding insertion, examples of which are described below, in conjunction with FIGS. 2-5.

Figure 2:
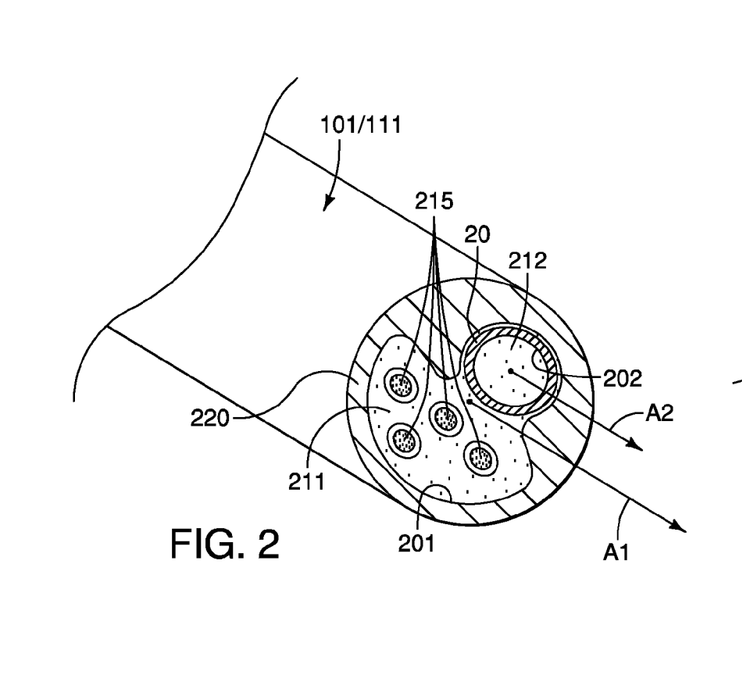
FIG. 2 is a cross-section perspective view of a lead body construction, according to a first group of embodiments.

FIG. 2 is a cross-section perspective view of a lead body construction, according to a first group of embodiments. FIG. 2 illustrates lead body 101/111 including an outer sheath 220, a first lumen 201, in which conductors 215 extend, and a second lumen 202 extending alongside first lumen 201; each of first and second lumens 201, 202 extend longitudinally within sheath 220 between proximal end 103/113 and distal end 105/115 of lead body 101/111 (FIG. 1). According to the illustrated embodiment, second lumen 202 is defined by an elongate tube 20 extending within a portion of first lumen 201, and a central longitudinal axis A2 of second lumen 202 is radially offset from a central longitudinal axis A1 of first lumen 201. While tube 20 is illustrated having a generally circular cross-section, other cross-section shapes can be employed.

FIG. 2 further illustrates a first filler 211 extending around conductors 215 within first lumen 201, and a second filler 212 extending within second lumen 202. According to exemplary embodiments, second filler 212 has a stiffness greater than that of first filler 211, and, with reference back to FIG. 1, second filler 212 extends along a proximally located limited length L2, preferably no greater than approximately two inches. Tube 20 may extend beyond length L2 or may have a length approximately equal to length L2.

Figure 3:
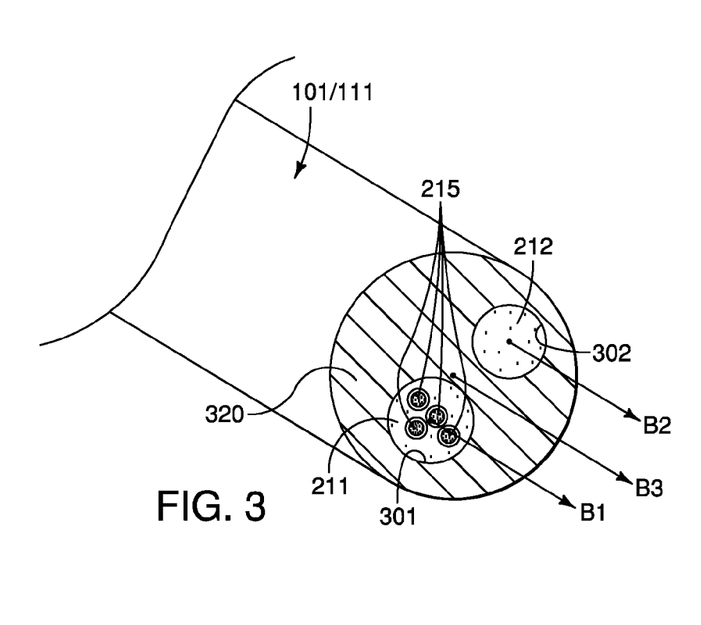
FIG. 3 is a cross-section perspective view of a lead body construction, according to a second group of embodiments.

FIG. 3 is a cross-section perspective view of a lead body construction, according to a second group of embodiments. FIG. 3 illustrates lead body 101/111 including an outer sheath 320, a first lumen 301, in which conductors 215 extend, and a second lumen 302 extending alongside first lumen 301; each of first and second lumens 301, 302 extend longitudinally within sheath 320 between proximal end 103/113 and distal end 105/115 of lead body 101/111 (FIG. 1). According to the illustrated embodiment, first and second lumens 301, 302 extend independent of one another within sheath 320, each having a central longitudinal axis B1, B2, respectively, being radially offset from the other and being radially offset from a central longitudinal axis B3 of sheath. FIG. 3 further illustrates first filler 211 extending around conductors 215 within first lumen 301, and second filler 212 extending within second lumen 302. Similar to the embodiments illustrated by FIG. 2, second filler 212 extends along a proximally located limited length L2 (FIG. 1).

With reference to FIGS. 2 and 3, first filler 211, being relatively flexible, to bend without kinking or cracking, may fill up to an entire length of first lumen 201/301 between proximal end 103/113 and distal end 105/115 of lead body 101/111 in order to provide support and/or electrical isolation for conductors 215, without significantly stressing conductors 215 and without significantly increasing a stiffness of lead body 101/111; while second filler 212, having a greater stiffness than first filler 211, being relatively rigid, provides added rigidity to lead body 101/111, along length L2, for example, between approximately three quarters of an inch and approximately two inches, in order to facilitate insertion of connector terminal 102/114. It should be appreciated that second filler 212, being contained in second lumen 202/302, is separated from conductors 215 and can thereby stiffen the proximal portion of lead body 101/111 without coming into contact with conductors 215, although this is not essential.

According to some embodiments, conductors 215 are cabled bundles of fine wires which may be drawn filled tubes (DFT), for example, silver-cored MP35N alloy, known to those skilled in the art. Conductors 215 may be covered, for example, via coating or extrusion, with an insulative jacket, for example fluoropolymer or polyimide, and, if the insulative jacket of each conductor 215 is sufficient to provide all the necessary electrical isolation for conductors 215, first filler 211 need not provide for electrical isolation therebetween; thus, first filler 211 may only extend along a limited length of lead body 101/111, like second filler 212, for example, along a length only slightly longer than L2 to provide some strain relief at a distal termination of second filler 212. Sheaths 220 and 320 may be formed, for example, via extrusion, from medical grade silicone rubber or polyurethane; tube 20 (FIG. 2) may likewise be formed from either medical grade silicone rubber or polyurethane, or from a fluoropolymer such as polytetrafluoroethylene (PTFE) or Ethylene TetrafluoroEthylene (ETFE).

According to some embodiments, first and second fillers 211, 212 comprise adhesive materials; preferably first filler 211 comprises a silicone medical adhesive and second filler 212 comprises a thermosetting epoxy adhesive. Second filler 212 may, alternatively, be a pre-formed component, for example, a metal or relatively rigid plastic insert, or, according to some embodiments, a combination of an adhesive material and an insert, embodiments of which will be described below. Each of fillers 211, 212, embodied as adhesive materials, may be dispensed, via syringe injection, into corresponding first and second lumens 201/301, 202/302, either before or after connector terminal 102/114 is assembled; likewise a pre-formed component, comprising all or part of second filler 212, may be inserted into second lumen 202/302 either before or after connector terminal 102/114 is assembled.

Figure 4A:
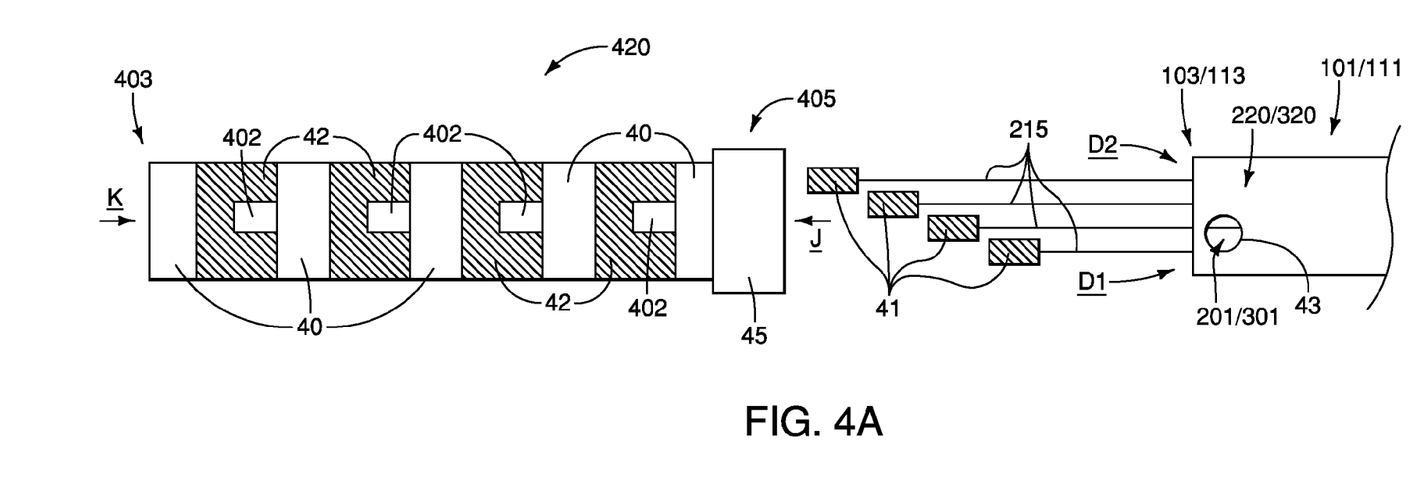
FIG. 4A is an exploded plan view of a portion of a lead assembly, according to some embodiments.
Figure 4B:
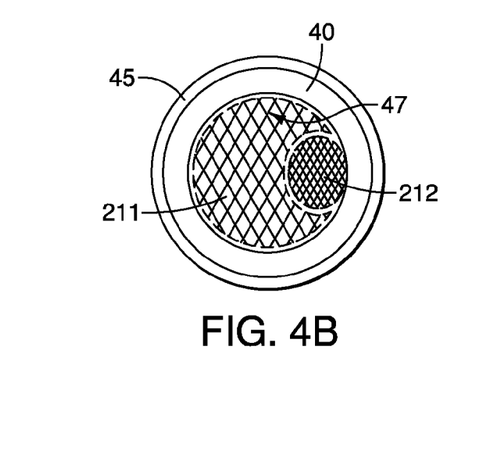
FIG. 4B is an end view of a connector terminal subassembly of the lead assembly shown in FIG. 4A, according to some embodiments.

FIG. 4A is an exploded plan view of a proximal portion of a lead assembly, either for adapter lead 100 or for stimulation lead 110, and FIG. 4B is an end view of a corresponding connector terminal subassembly 420, at a distal end 405 thereof, for either of connector terminals 102 and 114, according to some embodiments. FIGS. 4A-B illustrate connector terminal subassembly 420 including an insulative structure 40 on which conductive rings 42 are mounted, for example, via insert molding; structure 40 may be formed from a relatively rigid biocompatible plastic, for example, a 75D durometer polyurethane. According to the illustrated embodiment, conductors 215 are passed into a longitudinally extending lumen 47 of structure 40, per arrow J, such that a conductive component 41, which is coupled, for example, via crimping, to each conductor 215, may be inserted into a slot 402 of the corresponding conductive ring 42 for coupling thereto, for example, via laser welding, in order to form connector elements 106/117 (FIG. 1). FIGS. 4A-B further illustrate distal end 405 of connector terminal subassembly 420 including a mating feature or sleeve 45 for attaching proximal end 103/113 of lead body 101/111 to subassembly 420, for example, via adhesive or thermal bonding of sheath 220/320 within sleeve 45, according to an exemplary embodiment.

With reference to FIG. 4A, in conjunction with FIGS. 2-3, it may be appreciated that first filler 211 may be dispensed directly into first lumen 201/301, and second filler 212 directly into second lumen 202/302, each at proximal end 103/113, per arrows D1 and D2, respectively, prior to attaching proximal end 103/113 to subassembly 420. However, an optional port 43 is shown extending through a sidewall of sheath 220/320 for access to first lumen 201/301, so that first filler 211, for example, comprising silicone medical adhesive, may alternately be dispensed therethrough; another optional port may be provided for dispensing of second filler 212 into second lumen 202/302. With further reference to FIGS. 4A-B, lumen 47 of connector subassembly 420 may include an opening at a proximal end 403 thereof, so that one or both of fillers 211, 212 may be assembled, via lumen 47, per arrow K, into lead body 101/111 after connector terminal 102/114 is assembled, although this is not essential.

According to some preferred embodiments, either one or both of first and second fillers 211, 212 further extend into connector terminal 102/114, for example, as illustrated by dashed lines and cross-hatching in the end view of FIG. 4B. With reference back to FIG. 2, according to some embodiments, tube 20, which forms second lumen 202, extends proximally from sheath 220, of lead body 101/111, and into connector terminal 102/114, in order to contain second filler 212 therein, and to separate second filler 212 from first filler 211. First filler 211, particularly when embodied as a silicone medical adhesive, is preferably dispensed, via syringe injection, into first lumen 201/301 of lead body 101/111 and into lumen 47 of connector terminal subassembly 420, after conductors 215 are coupled, via conductive components 41, to rings 42. Second filler 212, either embodied as an epoxy adhesive, or as a pre-formed component, or as a combination thereof, may be assembled into lumen 47 either before or after the coupling of conductors 215, but, preferably, before the dispensing of first filler 211 into lumen 47.

Figure 5:
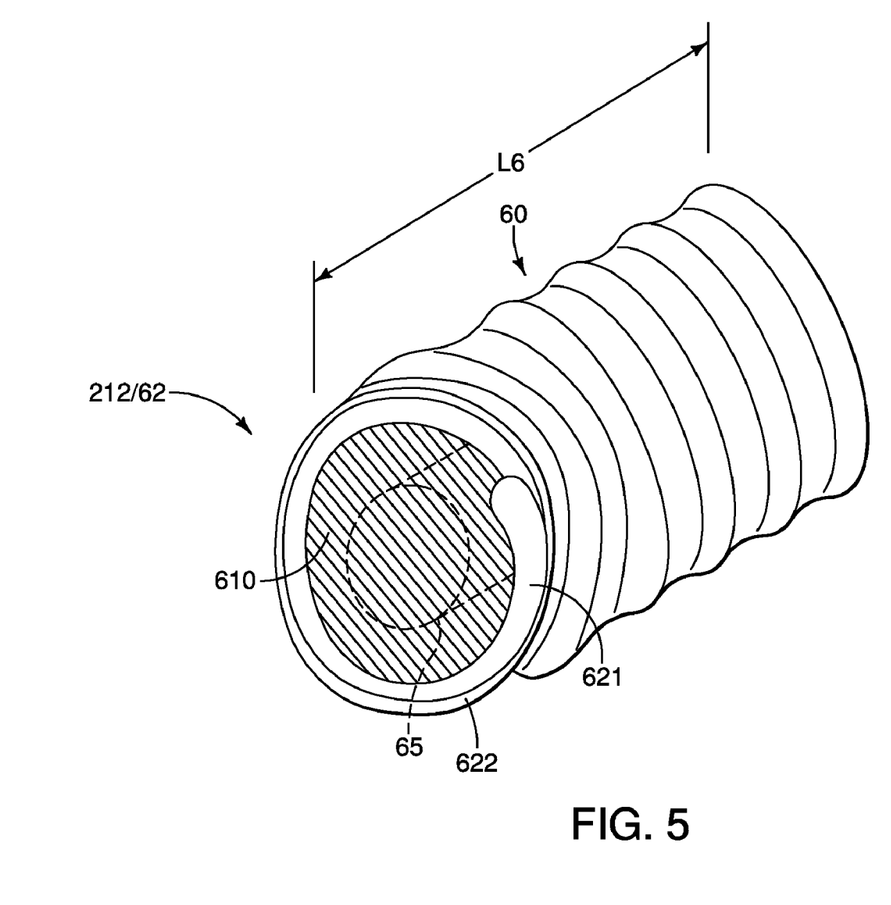
FIG. 5 is a perspective view of a filler component, according to some embodiments.

According to some embodiments, second filler 212 includes epoxy adhesive filling a pre-formed tubular insert, for example, tube 20 of FIG. 2, or tube 60, which is shown in FIG. 5. FIG. 5 is a perspective view of second filler 212 embodied as a pre-formed filler component 62, according to an exemplary embodiment. FIG. 5 illustrates filler component 62 including tube 60, epoxy adhesive 610, which fills at least a portion of a length L6 of tube 60, and an optional pre-formed reinforcing member 65, which is shown with dashed lines extending within tube 60. FIG. 5 further illustrates tube 60 including a coil member 621 surrounded by a polymer jacket 622, for example, a fluoropolymer tube that has been attached thereto via a heat shrink method known to those skilled in the art. With reference back to FIG. 1, length L6 of tube 60 may be limited so as not to extend from connector terminal 102/114, within lead body 101/111, distally past a distal termination of limited length L2, or length L6 may be longer to extend distally within lead body 101/111 beyond the distal termination of length L2.

According to some preferred methods, filler component 62 is assembled by first attaching jacket 622 about coil member 621, to form tube 60, and then by dispensing the epoxy adhesive 610, for example, by injecting, from a syringe, into tube 60. The epoxy adhesive 610 may be cured, within tube 60, at a temperature of approximately 150° F., for between approximately 12 and 24 hours, prior to inserting filler component 62, as second filler 212, into lumen 202/302 (FIGS. 2-3), and, for some embodiments, also into lumen 47 of connector terminal subassembly 420, for example, at proximal end 403 of subassembly 420, via arrow K (FIG. 4A), after connector terminal 102/114 is assembled. For those embodiments including optional reinforcing member 65, member 65 may be inserted into tube 60 either before or after adhesive 610 is injected; according to a preferred method step, member 65, for example, a metal wire insert having a length of approximately 1.5 inches and a diameter on the order of 0.010 inch, is inserted with a rotation into tube 60 immediately after the epoxy adhesive 610 is injected therein; the rotation may assure uniform coverage of member 65 with adhesive 610.

According to some alternate assembly methods, after connector terminal 102/114 is assembled to lead body 101/111, second filler 212, embodied as an epoxy adhesive, is dispensed, into second lumen 202/302 of sheath 220/320, from a syringe, via a needle coupled thereto, which needle has been passed, per arrow K, into lumen 47, from proximal end 403, for access into second lumen 202/302. After dispensing adhesive into second lumen 202/302, and as the syringe needle is retracted proximally within lumen 47, syringe may continue to dispense second filler 212 within lumen 47 of connector subassembly 420. In a like manner, following assembly of connector terminal 102/114, first filler 211, embodied as a silicone adhesive, may be dispensed from a syringe into first lumen 201/301, and optionally within lumen 47; alternatively, port 43 may provide access for the syringe needle to dispense first filler 211. According to those embodiments in which second filler 212 comprises a pre-formed component, either alone or in combination with the adhesive, the pre-formed component may be inserted into second lumen 202/302, via lumen 47, from proximal end 403, and may further extend into lumen 47, as previously described.

Figure 6:
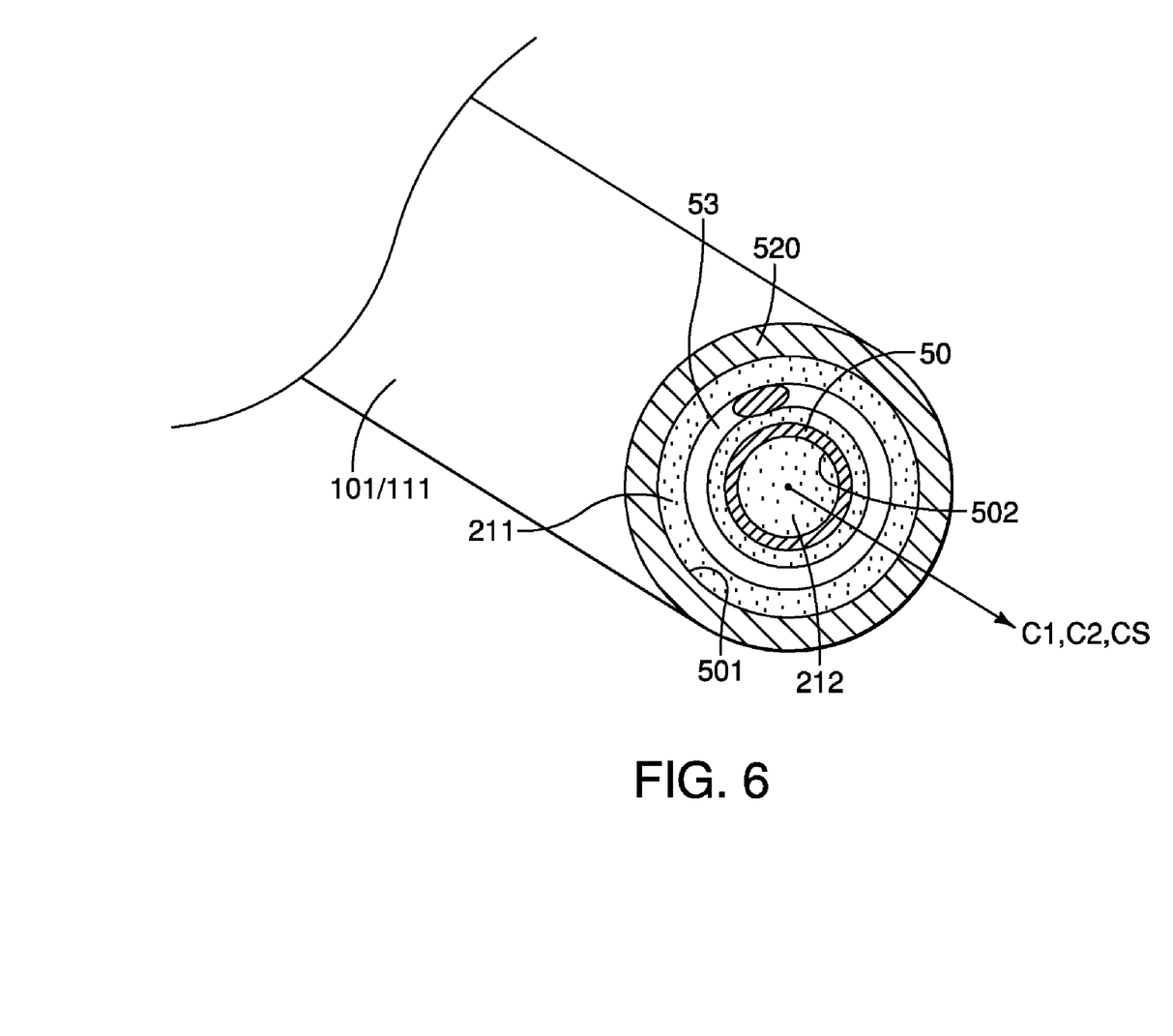
FIG. 6 is a cross-section perspective view of a lead body construction, according to a third group of embodiments.

FIG. 6 is a cross-section perspective view of a lead body construction, according to a third group of embodiments. FIG. 6 illustrates lead body 101/111 including an outer sheath 520, a first lumen 501, in which a multi-conductor coil 53 extends, and a second lumen 502 extending alongside and within first lumen 501; each of first and second lumens 501, 502 extend longitudinally within sheath 520 between proximal end 103/113 and distal end 105/115 of lead body 101/111 (FIG. 1). Those skilled in the art will appreciate that multi-conductor coil 53 includes a plurality of coiled conductor filars, each of which are individually insulated, for example, by a coating of polyimide, and that each coiled conductor filar electrically couples an electrode 118 to a corresponding connector element 107, for stimulation lead 110, or an electrical contact 107 to a corresponding connector element 106, for adapter lead 100.

According to the illustrated embodiment, second lumen 502 is formed by an elongate tube 50 extending approximately coaxially within first lumen 501, such that a central longitudinal axis C2 of second lumen 502 is approximately aligned with a central longitudinal axis C1 of first lumen 501. FIG. 6 further illustrates first filler 211 extending around multi-conductor coil 53 within first lumen 501, and second filler 212 extending within second lumen 502. With reference back to FIG. 1, second filler 212 preferably extends along proximally located limited length L2. Tube 50 may extend beyond length L2 or may have a length approximately equal to length L2. Like the embodiments described in conjunction with FIGS. 2-3, first filler 211 may provide support and/or additional electrical isolation for coil 53, either along a length approximately equal to limited length L2, or along a greater length, between proximal end 103/113 and distal end 105/115 of lead body 101/111, up to an entire length thereof, without significantly increasing a stiffness thereof, while second filler 212 provides added stiffness to lead body 101/111 along limited length L2 to facilitate insertion of connector terminal 102/114. Furthermore, for those embodiments employing the lead body construction of FIG. 6, first filler 211 and/or second filler 212 may further extend into connector terminal 102/114, as previously described in conjunction with FIGS. 4A-B.

In the foregoing detailed description, the invention has been described with reference to specific embodiments. However, it may be appreciated that various modifications and changes can be made without departing from the scope of the invention as set forth in the appended claims.

We claim:

1. An implantable medical electrical lead comprising: an elongate insulative lead body including a proximal end and a distal end; a plurality of conductors extending longitudinally within the lead body, from the proximal end to the distal end of the lead body; a connector terminal extending proximally from the proximal end of the lead body and coupled to the plurality of conductors; a first lumen extending longitudinally within the lead body, around the plurality of conductors and along a length of the lead body; a first filler within the first lumen, the first filler having a stiffness; a second lumen extending longitudinally within the lead body, wherein an axial cross section of the lead body includes the first and second lumens; a second filler within the second lumen, the second filler having a stiffness greater than the stiffness of the first filler, and the second filler extending along a limited length at the proximal end of the lead body.

2. The lead of claim 1, wherein the first and second lumens each include a central longitudinal axis that is radially offset from a central longitudinal axis of the lead body.

3. The lead of claim 1, wherein the lead body further includes a tube extending longitudinally within the first lumen to form the second lumen in which the second filler extends.

4. The lead of claim 3, wherein a central longitudinal axis of the second lumen is radially offset from a central longitudinal axis of the first lumen.

5. The lead of claim 1, wherein the limited length, along which the second filler extends, is no greater than approximately two inches.

6. The lead of claim 1, wherein the first filler comprises silicone adhesive.

7. The lead of claim 6, wherein he second filler comprises epoxy adhesive.

8. The lead of claim 1, wherein the second filler comprises epoxy adhesive.

9. The lead of claim 8, wherein the second filler further comprises a pre-formed component.

10. The lead of claim 1, wherein the second filler comprises a pre-formed component.

11. The lead of claim 10, wherein the pre-formed component comprises a coil member, a polymer jacket surrounding the coil member, and epoxy adhesive extending within the coil member.

12. The lead of claim 10, wherein the pre-formed component comprises epoxy adhesive and a pre-formed reinforcing member extending within the epoxy adhesive.

13. The lead of claim 1, wherein: the connector terminal includes a plurality of connector elements isolated from one another; each conductor of the plurality of conductors is coupled to a corresponding connector element of the plurality of connector elements; and the first filler isolates the plurality of conductors from one another within the lead body.

14. The lead of claim 1, wherein the second filler further extends into the connector terminal.

15. The lead of claim 14, wherein the second filler comprises epoxy adhesive.

16. The lead of claim 15, wherein the second filler further comprises a pre-formed component.

17. The lead of claim 14, wherein the second filler comprises a pre-formed component.

18. The lead of claim 17, wherein the pre-formed component comprises a coil member, a polymer jacket surrounding the coil member, and epoxy adhesive extending within the coil member.

19. The lead of claim 17, wherein the preformed component comprises epoxy adhesive and a pre-formed reinforcing member extending within the epoxy adhesive.

20. The lead of claim 1, further comprising a connector port extending distally from the distal end of the lead body and coupled to the connector terminal via the plurality of conductors.

21. The lead of claim 1, further comprising an electrode array extending distally from the distal end of the lead body and coupled to the connector terminal via the plurality of conductors.

22. A method for assembling a proximal portion of a medical electrical lead, the method comprising: forming a relatively rigid filler by dispensing an adhesive material into a tube; inserting the relatively rigid filler into a limited length of an elongate insulative body of the lead, at a proximal end thereof; dispensing a relatively flexible filler into the body, at the proximal end thereof and alongside the limited length for the relatively rigid filler; and attaching a connector terminal subassembly to the proximal end of the body.

23. The method of claim 22, further comprising attaching a polymer jacket about a coil member to form the tube into which the adhesive material is dispensed.

24. The method of claim 22, wherein forming the relatively rigid filler further comprises inserting a pre-formed reinforcing member into the tube after dispensing the adhesive material therein.

25. The method of claim 22, further comprising inserting the relatively rigid filler into a lumen of the connector terminal subassembly.

26. The method of claim 22, further comprising dispensing the relatively flexible filler into the lumen of a connector terminal subassembly.

27. An implantable medical electrical lead system comprising: an implantable medical electrical stimulation lead comprising: an elongate insulative stimulation lead body including a proximal end and a distal end; a stimulation lead connector extending proximally from the proximal end of the stimulation lead body; a stimulation lead electrode array extending distally from the distal end of the stimulation lead body; and a plurality of stimulation lead conductors extending within the stimulation lead body, from the proximal end to the distal end thereof, the plurality of stimulation lead conductors coupling the stimulation lead connector to the stimulation lead electrode array; and an implantable medical electrical adapter lead comprising: an elongate insulative adapter lead body including a proximal end and a distal end; a connector terminal extending proximally from the proximal end of the adapter lead body; a connector port extending distally from the distal end of the adapter lead body; a plurality of adapter lead conductors extending longitudinally within the adapter lead body, from the proximal end to the distal end of the adapter lead body, the plurality of adapter lead conductors coupling the connector terminal to the connector port; a first lumen extending longitudinally within the adapter lead body, around the adapter lead conductors and along a length of the adapter lead body; a first filler within the first lumen, the first filler having a stiffness; a second lumen extending longitudinally within the adapter lead body, wherein an axial cross section of the lead body includes first and second lumens; a second filler within the second lumen, the second filler having a stiffness greater than the stiffness of the first filler, and the second filler extending along a limited length at the proximal end of the adapter lead body; wherein the connector port of the adapter lead is adapted to couple with the stimulation lead connector for electrical coupling of the stimulation lead electrode array with the connector terminal of the adapter lead.

28. The lead system of claim 27, wherein the first and second lumens each include a central longitudinal axis that is radially offset from a central longitudinal axis of the adapter lead body.

29. The lead system of claim 27, wherein the adapter lead body further includes a tube extending longitudinally within the first lumen to form the second lumen in which the second filler extends.

30. The lead system of claim 29, wherein a central longitudinal axis of the second lumen is radially offset from a central longitudinal axis of the first lumen.

31. The lead system of claim 27, wherein the limited length, along which the second filler extends, is no greater than two inches.

32. The lead system of claim 27, wherein the first filler comprises silicone adhesive.

33. The lead system of claim 32, wherein the second filler comprises epoxy adhesive.

34. The lead system of claim 27, wherein the second filler comprises epoxy adhesive.

35. The lead system of claim 34, wherein the second filler further comprises a pre-formed component.

36. The lead system of claim 27, wherein the second filler comprises a pre-formed component.

37. The lead system of claim 36, wherein the pre-formed component comprises a coil member, a polymer jacket surrounding the coil member, and epoxy adhesive extending within the coil member.

38. The lead system of claim 36, wherein the preformed component comprises epoxy adhesive and a pre-formed reinforcing member extending within the epoxy adhesive.

39. The lead system of claim 27, wherein: the stimulation lead connector includes a plurality of first connector elements isolated from one another; the stimulation lead electrode array includes a plurality of electrodes isolated from one another; the plurality of stimulation lead conductors are isolated from one another within the stimulation lead body; each stimulation lead conductor of the plurality of stimulation lead conductors couples a corresponding first connector element of the plurality of first connector elements to a corresponding electrode of the plurality of electrodes; the connector terminal of the adapter lead includes a plurality of second connector elements isolated from one another; the connector port of the adapter lead includes a plurality of electrical contacts isolated from one another and positioned to make contact with a corresponding first connector element of the plurality of connector elements of the stimulation lead connector, when the connector port is coupled with the stimulation lead connector; each adapter lead conductor of the plurality of adapter lead conductors couples a corresponding second connector element of the connector terminal to a corresponding electrical contact of the connector port; and the first filler isolates the plurality of adapter lead conductors from one another within the adapter lead body.

40. The lead system of claim 27, wherein the second filler further extends into the connector terminal of the adapter lead.

41. The lead system of claim 40, wherein the second filler comprises epoxy adhesive.

42. The lead system of claim 41, wherein the second filler further comprises a pre-formed component.

43. The lead system of claim 40, wherein the second filler comprises a pre-formed component.

44. The lead system of claim 43, wherein the pre-formed component comprises a coil member, a polymer jacket surrounding the coil member, and epoxy adhesive extending within the coil member.

45. The lead system of claim 43, wherein the preformed component comprises epoxy adhesive and a pre-formed reinforcing member extending within the epoxy adhesive.

46. An implantable medical electrical lead comprising: an elongate insulative lead body including a proximal end and a distal end; a plurality of conductors extending longitudinally within the lead body, from the proximal end to the distal end of the lead body; a connector terminal extending proximally from the proximal end of the lead body and coupled to the plurality of conductors; a first filler extending longitudinally within the connector terminal and the lead body, around the plurality of conductors and along a length of the lead body, the first filler having a stiffness; a second filler extending longitudinally alongside the first filler within the connector terminal and the lead body, the second filler comprising a pre-formed component and epoxy adhesive extending therein, the second filler having a stiffness greater than the stiffness of the first filler, and the second filler extending along a limited length of the lead body.

* * * * *

UNITED STATES PATENT AND TRADEMARK OFFICE
CERTIFICATE OF CORRECTION

| | | |
|---|---|---|
| PATENT NO. | : 7,974,704 B2 | Page 1 of 1 |
| APPLICATION NO. | : 11/843021 | |
| DATED | : July 5, 2011 | |
| INVENTOR(S) | : Alexander et al. | |

It is certified that error appears in the above-identified patent and that said Letters Patent is hereby corrected as shown below:

Patent Column 7, line 60 (claim 7): ", wherein he second" should read -- wherein the second --.

Signed and Sealed this
Third Day of April, 2012

David J. Kappos
*Director of the United States Patent and Trademark Office*